(12) United States Patent
Drake et al.

(10) Patent No.: US 10,262,556 B2
(45) Date of Patent: Apr. 16, 2019

(54) APPARATUS AND METHODS FOR VISUAL DEMONSTRATION OF DENTAL EROSION ON SIMULATED DENTAL MATERIALS

(71) Applicant: The Procter & Gamble Company, Cincinnati, OH (US)

(72) Inventors: Phillip Asa Drake, Mason, OH (US); Ruzhan Peng, Mason, OH (US); George Endel Deckner, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 10 days.

(21) Appl. No.: 15/299,495

(22) Filed: Oct. 21, 2016

(65) Prior Publication Data

US 2017/0039893 A1   Feb. 9, 2017

Related U.S. Application Data

(63) Continuation of application No. 14/710,620, filed on May 13, 2015, now abandoned, which is a (Continued)

(51) Int. Cl.
*G09B 23/00*   (2006.01)
*G09B 23/28*   (2006.01)
(Continued)

(52) U.S. Cl.
CPC .......... *G09B 23/283* (2013.01); *A61K 6/0017* (2013.01); *G09B 19/0084* (2013.01); *B05D 1/185* (2013.01); *B05D 2350/65* (2013.01)

(58) Field of Classification Search
CPC .......................... G09B 23/283; G09B 19/0084
See application file for complete search history.

(56) References Cited

U.S. PATENT DOCUMENTS 5,123,844 A * 6/1992 Wakai .................. A61C 8/0012
                                                        433/173
5,441,536 A   8/1995 Aoki Hideki et al.
(Continued)

OTHER PUBLICATIONS

All Office Actions in Case 114406MC, U.S. Appl. No. 14/710,620, filed May 13, 2015—See Private Pair.

*Primary Examiner* — Alvin A Hunter
*Assistant Examiner* — Alyssa Hylinski
(74) *Attorney, Agent, or Firm* — Parker D. McCrary; Alexandra S. Anoff (57) ABSTRACT

Comparative effectiveness of various oral care products such as dentifrices on preventing dental erosion may be demonstrated using simulated enamel. A substrate is prepared. A mineral layer to simulate dental enamel is nucleated by solution growth on the substrate surface. Alternatively, the mineral layer may be nucleated on a template comprising a self-assembled monolayer formed on a gold layer deposited on the substrate surface. The mineral layer may comprise a homogeneous layer of hydroxyapatite or a thin veneer of hydroxyapatite on a layer of amorphous calcium phosphate. The simulated enamel is then optionally treated with an oral care product and subjected to an acid challenge. The amount of mineral layer remaining after the acid challenge illustrates the effectiveness or non-effectiveness of the oral care product at preventing dental erosion.

5 Claims, 4 Drawing Sheets

Related U.S. Application Data continuation of application No. 12/874,683, filed on Sep. 2, 2010, now Pat. No. 9,087,457.

(60) Provisional application No. 61/239,809, filed on Sep. 4, 2009.

(51) Int. Cl.
*G09B 19/00* (2006.01)
*A61K 6/00* (2006.01)
*B05D 1/18* (2006.01)

(56) References Cited

U.S. PATENT DOCUMENTS

| | | | |
|---|---|---|---|
| 5,989,031 A * | 11/1999 | Kura | A61C 13/09 264/19 |
| 6,207,218 B1 * | 3/2001 | Layrolle | A61F 2/30767 427/2.24 |
| 6,280,789 B1 | 8/2001 | Rey et al. | |
| 9,087,457 B2 * | 7/2015 | Drake | A61K 6/0017 |
| 2003/0016442 A1 | 1/2003 | Masuda | |
| 2003/0180687 A1 * | 9/2003 | Mrotzek | A61C 19/10 433/202.1 |
| 2006/0121180 A1 * | 6/2006 | Gertner | A61F 2/82 427/2.1 |
| 2007/0128762 A1 * | 6/2007 | Aizenberg | A61K 6/033 438/99 |
| 2007/0212449 A1 * | 9/2007 | Shamsuddin | A23L 2/52 426/74 |
| 2007/0213832 A1 * | 9/2007 | Wen | A61F 2/4455 623/23.5 |
| 2008/0220233 A1 * | 9/2008 | Kjellin | B82Y 30/00 428/220 |
| 2009/0123516 A1 * | 5/2009 | Agrawal | B82Y 30/00 514/1.1 |
| 2010/0016985 A1 * | 1/2010 | Rabiei | A61K 6/08 623/23.6 |
| 2015/0243191 A1 | 8/2015 | Drake et al. | |

* cited by examiner

APPARATUS AND METHODS FOR VISUAL DEMONSTRATION OF DENTAL EROSION ON SIMULATED DENTAL MATERIALS

BACKGROUND OF THE INVENTION

Embodiments described herein are directed generally to apparatus and methods for providing a visual demonstration of dental erosion.

Dental erosion is the dissolution of the tooth surface caused by acids of non-bacterial origin. The source of the acid may be gastric fluids (perimolysis) caused by a medical condition such as gastroesophageal reflux or bulimia. More commonly, erosion is caused by dietary sources of acid, such as sports drinks, certain soft drinks, fruits, and fruit juices. Estimates of prevalence vary widely and differ significantly by geography, but the incidence of clinically observable erosion may be as high as 60% for children in some Western countries.

Dental cleaning products continually are developed with active ingredients that improve in effectiveness toward preventing dental erosion. However, there remains a need to demonstrate the increased effectiveness of new products to the general public and dental professionals to encourage the use of such products.

SUMMARY OF THE INVENTION

The example embodiments shown and described herein relate to a demonstration model comprising a simulated dental enamel layer, to methods for preparing a demonstration model comprising a simulated dental enamel layer, and to methods for providing a visual demonstration of dental erosion by using such a demonstration model. In example demonstration methods, thin layers of various mineral phases that compose dentine and enamel may be grown on a substrate, using charged surfaces to template mineral formation in solutions of controlled composition and temperature. The mineral phases may be treated with one or more selected dentifrices and subjected to challenges simulating actual causes of dental erosion. The challenged layers thereby illustrate the efficacies of the selected dentifrices at preventing dental erosion.

In accordance with one embodiment, a demonstration model is provided. The demonstration model comprises a planar or three-dimensional substrate. The substrate may be a solid substrate, and may comprise a material such as, for example, silica. A top surface of the substrate may be coated with a simulated dental enamel layer. Example layers of simulated dental enamel may comprise hydroxyapatite. The hydroxyapatite may be a homogeneous layer on the substrate or a veneer layer on top of a layer of amorphous calcium phosphate formed on the substrate. Alternatively, the simulated dental enamel layer may be formed on a self-assembled monolayer such as, for example, a monolayer comprising a thiol compound, that is formed on a thin layer of gold coated on the top surface of the substrate.

In accordance with another embodiment, a method for preparing a demonstration model is provided. First, a planar or three-dimensional substrate is provided. The substrate may comprise a clean surface of a material such as, for example, a molded polymer article, a polymer film, a polymer tape, silica, quartz, or glass. A simulated dental enamel layer may be applied to the substrate surface by placing the substrate in an aqueous solution comprising a calcium salt and a phosphate salt until a mineral layer forms on a top surface of the substrate. Example simulated dental enamel layers may comprise hydroxyapatite in the form of a single coating or in the form of a veneer layer on top of a coating of amorphous calcium phosphate. One or more coloring agents may be added to at least one of the amorphous calcium phosphate layer and the simulated dental enamel layer.

In accordance with yet another embodiment, a method for preparing a demonstration model may comprise providing a planar or three-dimensional substrate coated with a thin layer of gold. A charged, self-assembled monolayer may be formed on the gold by exposing the thin layer of gold to a compound such as, for example, a carboxylated thiol. A simulated dental enamel layer may be applied on the self-assembled monolayer. Example simulated dental enamel layers may comprise hydroxyapatite in the form of a single coating or in the form of a veneer layer on top of a coating of amorphous calcium phosphate.

In accordance with yet another embodiment, a method for demonstrating dental erosion may comprise providing a demonstration model prepared according to other embodiments shown and described herein. The layer of simulated enamel present on the demonstration materials may be untreated or may be treated with at least one oral care product. The materials may be rinsed. Thereupon, the treated simulated enamel may be subjected to an erosion challenge. The erosion challenge may comprise exposing the demonstration materials to a corrosive agent such as dilute citric acid. After the erosion challenge, the physical structure of the resulting film will illustrate clearly the effect of the erosion challenge on the original layer of simulated enamel. The effect may be evaluated visually or by using appropriate instrumentation. The method may be repeated in multiple trials using various oral care products, and the results from each trial may be compared to illustrate the comparative efficacies of each product, whereby the most effective oral care products will be expected to show decreased amounts of erosion.

BRIEF DESCRIPTION OF THE DRAWINGS

Though the specification concludes with claims particularly pointing out and distinctly claiming the invention, it is believed that the present invention will be better understood from the following description taken in conjunction with the accompanying drawings in which:

DETAILED DESCRIPTION OF THE INVENTION

All percentages and ratios used in this detailed description are by weight of total composition, unless otherwise indicated. Unless otherwise indicated, all percentages, ratios, and levels of ingredients are based on the actual amount of the ingredient and do not include solvents, fillers, or other materials with which the ingredient may be combined to form a commercial product.

Terms that are not expressly defined in this patent are to be interpreted to the broadest scope of their plain or ordinary meaning. A term is considered expressly defined in this patent only if phrasing similar to "the term X means Y . . . " incorporates the term. It will be understood that an expressly defined term X is defined according to the provided definition Y unless otherwise specified.

No statement in any section of this patent outside the claims is to be construed as implied intent to limit the meaning of any term within the claims. Even if reference to a term outside the claims is consistent with only a single meaning of a term, it is not intended or implied that the term be limited to the single meaning when the term is recited within a claim. In such instances, use of the single meaning outside the claims is intended for the sake of clarity only.

Unless a claim limitation is defined by reciting the word "means" and a function, without the recital of any structure, it is not intended that the scope of the claim limitation be interpreted in accordance with 35 U.S.C. § 112, sixth paragraph.

No term is intended to be essential to the present invention unless so stated. Furthermore, terms such as "preferably," "generally," "commonly," and "typically" are not intended to limit the scope of the claimed invention or to imply that certain features are critical, essential, or even important to the structure or function of the claimed invention. Rather, these terms are intended only to highlight alternative or additional features that may or may not be utilized in a particular embodiment of the present invention.

For quantities, use of the term "substantially" is intended in consideration that quantitative comparisons, values, measurements, or other representations possess inherent degrees of uncertainty. In this sense, "substantially" broadens the scope of quantities to encompass values within the inherent margin of error for measuring or determining the quantities. The term "substantially" also is utilized to represent the degree by which a quantitative representation may vary from a stated reference without resulting in a change in the basic function of the subject matter at issue.

The term "compatible" in reference to an additional ingredient of a composition means that the additional ingredient can be commingled with other ingredients of the composition without causing any interaction that substantially reduces the composition's stability, its efficacy, or both.

The term "dentifrice" means a composition used to treat the surfaces of the oral cavity. The dentifrice may comprise one or more components. Each component has phase characteristics that may be the same as or different from those of the other components. Example phase characteristics of dentifrices and dentifrice components include, but are not limited to pastes, gels, powders, and liquids. The dentifrice may be in any desired form, such as deep-striped, surface-striped, multilayered, a gel surrounding a paste, a sheath/core arrangement, a co-extruded sheath/core arrangement, or any combination thereof. When packaged, for example, as an oral care product, one or more components of a multi-component dentifrice may be contained in a physically separated compartment of a dispenser and dispensed side-by-side; one or more components may be striped together without physical separation; or some components may be contained separately and some components may be striped together.

The term "oral care product" means a product that, in the ordinary course of usage, can be retained in the oral cavity for purposes of oral activity. The oral activity may arise from contact of the oral care product with selected dental surfaces (e.g., teeth), oral tissues (e.g., gums), or both. Typically, oral care products are used for purposes such as to clean teeth by removing dental plaque; to prevent formation of dental calculus; to prevent disorders such as caries (tooth decay), periodontitis, and gingivitis; and to eliminate and prevent oral malodor, halitosis, and staining. Examples of oral care products may include, but not be limited to, toothpastes, dentifrices, tooth gels, sub-gingival gels, foams, mouth rinses, denture products, mouth sprays, lozenges, chewable tablets, chewing gums, and strips or films for direct application or attachment to oral surfaces, including any hard or soft oral tissues. However, the term "oral care product" should not be construed narrowly as referring only to formulations readily intended for consumer use. Rather, it will be understood that "oral care product" also encompasses any compound or mixture of compounds suitable for use as active or inactive ingredients of a consumer product, provided they can be retained in the oral cavity for purposes of oral activity.

A demonstration model may comprise a substrate and a simulated dental enamel layer disposed over a first side of the substrate. As used herein, "simulated dental enamel layer" means a layer of a material, i.e., of a simulated dental enamel, having physical and chemical properties substantially similar to those of enamel layers of animal teeth such as, for example, human teeth, dog teeth, or bovine teeth. The term "disposed over" means that the simulated dental enamel layer is in a relative position over the substrate and may be in direct contact with a surface of the substrate or may be in direct contact with a layer interposed between the substrate and the simulated dental enamel layer. Any substrate may be used that can support a simulated dental enamel layer. The substrates may be chosen to be essentially inert to a selected acid challenge solution, described below in detail. As used herein, the term "essentially inert" with respect to the substrate means that the substrate is not visibly etched, clouded, or dissolved by the acid challenge solution when the substrate is immersed in the acid challenge solution at a temperature of at least 37° C. for a period longer than a typical acid challenge, described below, for example 10 minutes to 24 hours. The substrate may be a solid substrate and may be planar or three-dimensional. Non-limiting examples of solid substrates include clean silica surfaces such as quartz or fused silica. Glasses such as borosilicate glasses are also appropriate solid substrates. Further examples of solid substrates include polymers, including, for example, molded polymer articles, polymer films, or polymer tapes. The substrate may comprise a polymer tape having an adhesive on one side. In further examples, the substrate may be coated with a metal layer, and a self-assembled monolayer may be grown on the metal layer. As a particular example, a gold layer may be grown on a silica substrate, and a self-assembled monolayer may be grown on the gold layer by exposing the gold layer to a carboxylated thiol.

Though any material having appreciable solubility in an acid may be used to demonstrate dental erosion, in preferred embodiments the simulated dental enamel layer comprises one or more materials approximating the physical behavior and chemical composition of the enamel layers of animal teeth. The thicknesses of the simulated enamel layers may vary. Preferably, the simulated dental enamel layer is sufficiently thick so as to provide sharp visual contrast between the top surface of a clean substrate and the top surface of a simulated enamel layer. The sharp visual contrast, in turn, may provide a more striking demonstration model for use in demonstrating efficacies of oral care products.

As an example, the simulated dental enamel layer may comprise hydroxyapatite. The hydroxyapatite may be disposed on the substrate, for example, in direct contact with and coating at least a portion of a surface of the substrate. Alternatively, one or more additional layers, described in detail below, may be interposed between the substrate and the hydroxyapatite. The simulated dental enamel layer may comprise a substantially homogeneous layer such as, for example, a substantially homogeneous layer of hydroxyapatite. As used here, the simulated dental enamel layer is substantially homogeneous if it contains less than 10% by weight of crystalline or non-crystalline impurities, based on the weight of the layer. Hydroxyapatite is a crystalline form of calcium phosphate, typically described by the chemical formula $Ca_5(PO_4)_3(OH)$ or $Ca_{10}(PO_4)_6(OH)_2$, the second formula denoting a crystal unit cell comprising two identical units of $Ca_5(PO_4)_3(OH)$. It will be understood, however, that the typical formula for hydroxyapatite is not presented with the intent of limiting the chemical structure of the simulated enamel to strictly stoichiometric compounds. Moreover, it will be understood that any form of crystalline calcium phosphate mineral approximating the physical characteristics of dental enamel is suitable for use as the simulated dental enamel layer.

It will be understood that the following specific example embodiments of demonstration models are not intended to be limiting and that many variations and modifications will be apparent to the person of ordinary skill in the art. Referring now to FIGS. 1-4, specific, non-limiting example embodiments of demonstration models include a single-layer demonstration model 1, shown in FIG. 1; bilayer demonstration model 2, shown in FIG. 2; a single-layer-on-monolayer demonstration model 3, shown in FIG. 3; and a bilayer-on-monolayer demonstration model 4, shown in FIG. 4.

Figure 1:
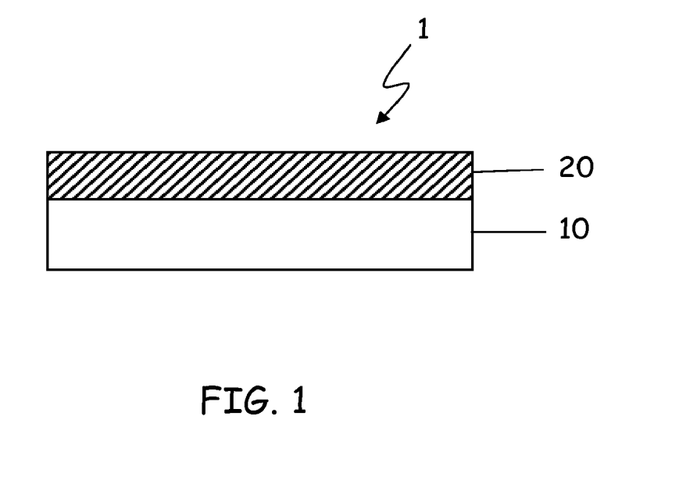
FIG. 1 is a side view of an example demonstration model comprising a substrate and a simulated dental enamel layer disposed over the substrate.

Referring to FIG. 1, a single-layer demonstration model 1 may comprise a substrate 10 and a simulated dental enamel layer 20 disposed over the substrate 10. Here, the simulated dental enamel layer 20 is shown in direct contact with a substrate surface 11. The simulated dental enamel layer 20 may comprise hydroxyapatite, for example, and may be substantially homogeneous, such as with a substantially homogeneous layer of hydroxyapatite. As nonlimiting examples, the simulated dental enamel layer 20 may have a thickness from about 10 A to about 500 µm, alternatively from about 10 A to about 250 µm, alternatively from about 10 A to about 100 µm, alternatively from about 10 A to about 50 µm, alternatively from about 10 A to about 10 µm, alternatively from about 10 A to about 1 µm, alternatively from about 10 A to about 500 nm, alternatively from about 10 A to about 100 nm, or alternatively from about 10 A to about 10 nm. Alternatively or in addition to hydroxyapatite, the simulated dental enamel layer 20 may comprise minerals including, but not limited to, fluoridated hydroxyapatite, fluorapatite, chlorapatite, or combinations thereof.

Figure 2:
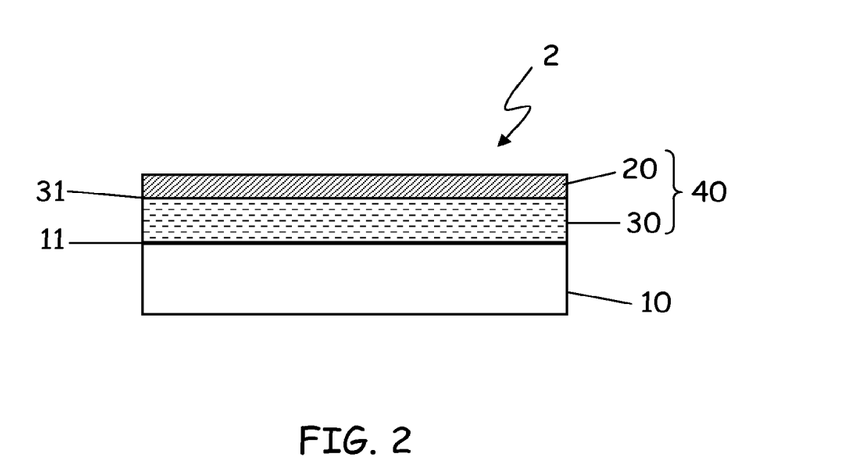
FIG. 2 is a side view of an example demonstration model having an enhanced bilayer structure, in which a fast-soluble layer is interposed between the substrate and the simulated enamel layer.

Referring to FIG. 2, a bilayer demonstration model 2 is shown, wherein a fast-dissolving layer 30 is interposed between the substrate 10 and the simulated dental enamel layer 20. The combination of the fast-dissolving layer 30 and the simulated dental enamel layer 20 results in an enhanced bilayer structure 40. Thus, the enhanced bilayer structure 40 may comprise two layers: the fast-dissolving layer 30 disposed on a substrate surface 11, and the simulated dental enamel layer 20 disposed on a fast-dissolving layer surface 31 opposite the substrate 10. The simulated dental enamel layer 20 may comprise, for example, hydroxyapatite. The fast-dissolving layer 30 may be chosen from one or more minerals or other material suitable for growth of simulated dental enamel layers thereon. Preferably, the fast-dissolving layer 30 comprises one or more materials known to dissolve more quickly in an acid solution than hydroxyapatite would dissolve in the same solution. It may be desirable for the fast-dissolving layer 30 to comprise a precursor compound to simulated dental enamel layer 20. As used here, a precursor compound to simulated dental enamel is a compound that can be chemically converted to the simulated dental enamel by reacting the precursor with one or more reagents or by simply heating the precursor compound. If simulated dental enamel layer 20 comprises hydroxyapatite, for example, fast dissolving layer 30 may comprise an amorphous calcium phosphate, a precursor to hydroxyapatite.

The fast-dissolving layer 30 may be in direct contact with the substrate surface 11. In one example embodiment, the simulated dental enamel layer 20 may be a veneer layer comprising hydroxyapatite. When the simulated dental enamel layer 20 is a veneer layer, a substantially greater portion of the thickness of the enhanced bilayer structure 40 is derived from the thickness of the fast-dissolving layer 30 than is derived from the thickness of the simulated dental enamel layer 20. Example thicknesses of fast-dissolving layer 30 include from about 10 A to about 500 µm, alternatively from about 10 A to about 250 µm, alternatively from about 10 A to about 100 µm, alternatively from about 10 A to about 50 µm, alternatively from about 10 A to about 10 µm, alternatively from about 10 A to about 1 µm, alternatively from about 10 A to about 500 nm, alternatively from about 10 A to about 100 nm, alternatively from about 10 A to about 10 nm. Example thicknesses of the simulated dental enamel layer 20 include from about 10 A to about 500 µm, alternatively from about 10 A to about 250 µm, alternatively from about 10 A to about 100 µm, alternatively from about 10 A to about 50 µm, alternatively from about 10 A to about 10 µm, alternatively from about 10 A to about 1 µm, alternatively from about 10 A to about 500 nm, alternatively from about 10 A to about 100 nm, alternatively from about 10 A to about 10 nm.

Figure 3:
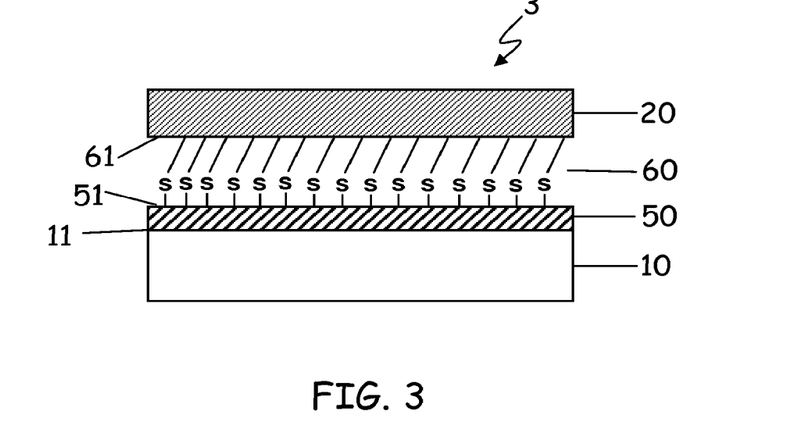
FIG. 3 is a side view of an example demonstration model comprising a substrate and a simulated dental enamel layer disposed over the substrate, wherein a self-assembled monolayer grown on a metal layer is interposed between the substrate and the simulated enamel layer.

Referring to FIG. 3, a single-layer-on-monolayer demonstration model 3 comprises in addition to the simulated dental enamel layer 20 a metal layer 50 having a self-assembled monolayer 60 formed thereon. The metal layer 50 may be in direct contact with a substrate surface 11 of substrate 10. The self-assembled monolayer 60 is connected to a metal surface 51 of the metal layer 50 opposite the substrate 10. A simulated dental enamel layer 20 is disposed on a monolayer surface 61 of the self-assembled monolayer 60, opposite metal layer 50. The simulated dental enamel layer 20 may comprise hydroxyapatite. The metal layer 50 may comprise any metal suitable for growth of a self-assembled monolayer on a surface of the metal. For example, the metal layer 50 may comprise gold or a gold alloy. The self-assembled monolayer 60 may comprise organic-chain molecules having a first reactive end bonded to the metal layer 50, an organic chain extending above the surface of the metal layer 50, and a second reactive end with a charged group suitable for forming a nucleation template, onto which the simulated dental enamel layer 20 may be grown or bonded. In example embodiments, the first reactive end may comprise a thiol, the organic chain may comprise an alkyl chain of about 3 to about 30 carbon atoms, and the second reactive end may comprise a charged group such as, for example, a carboxyl group, a sulfonate group, a phosphate group, or a quaternary amine Example simulated dental enamel layer 20 may have a thickness from about 10 A to about 500 µm. Example metal layer 50 may have a thickness from about 10 A to about 1000 A.

Figure 4:
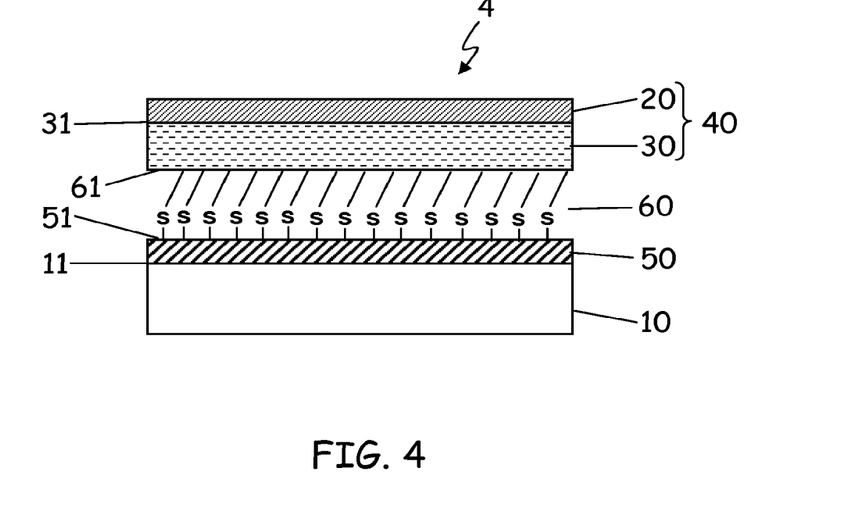
FIG. 4 is a side view of an example demonstration model comprising an enhanced bilayer structure grown on a self-assembled monolayer formed on a metal layer deposited on the substrate.

Referring to FIG. 4, a bilayer-on-monolayer demonstration model 4 may comprise metal layer 50, which may be disposed on a substrate surface 11 of substrate 10. A self-assembled monolayer 60 may be formed on a metal-layer surface 51 of metal layer 50, opposite substrate 10. An enhanced bilayer structure 40 may be disposed on a monolayer surface 61 of self-assembled monolayer 60, opposite metal layer 50. Enhanced bilayer structure 40 may comprise two layers: a fast-dissolving layer 30 that may be disposed on the self-assembled monolayer 60, and a simulated dental enamel layer 20 that may be disposed on a fast-dissolving layer surface 31 opposite the self-assembled monolayer 60. Simulated dental enamel layer 20 may comprise, for example, hydroxyapatite. Fast-dissolving layer 30 may comprise a precursor compound to simulated dental enamel layer 20. If simulated dental enamel layer 20 comprises hydroxyapatite, for example, fast-dissolving layer 30 may comprise an amorphous calcium phosphate, a precursor to hydroxyapatite. Simulated dental enamel layer 20 may be a veneer layer, more particularly a thin veneer layer, which may comprise hydroxyapatite. Example fast-dissolving layer 30 may have a thickness from about 10 A to about 500 flm. Example simulated dental enamel layer 20 may have a thickness from about 10 A to about 500 µm. Example metal layer 50 may have a thickness in the range of about 10 A to about 1000 A.

In all types of demonstration models, such as the example demonstration models described above, enhanced visual contrast between the simulated dental enamel layer and the bare substrate may be achieved through the addition of one or more coloring agents to one or more layers of the demonstration model. Example coloring agents include, but are not limited to dyes, pigments, opacifiers, combinations thereof, and any other additive capable of imparting a color to the simulated dental enamel layer, and/or any additional layers. A coloring agent may be dispersed uniformly throughout the thickness of the layered demonstration model or any individual layer of such model. Alternatively, a plurality of coloring agents of varying shades or hues may be dispersed in a graded manner through the thickness of the layered demonstration model or any individual layer of such model. In a graded dispersion, for example, coloring agents of lighter shades or hues are prevalent toward a bottom portion of the demonstration model, nearer the substrate, and coloring agents of darker shades or hues are prevalent toward a top portion of the demonstration model, farthest from the substrate. The graded structure also may be reversed, with the lighter shades or hues in the top portion and the darker shades or hues in the bottom portion. As used herein, "shade" refers to the depth of a given color. For example, "light blue" and "dark blue" would represent two different shades. The term "shade" also may apply to non-colors such as gray. As used herein, "hue" refers to the identity of the color itself. Thus, "red" and "blue" refer to different hues.

Example demonstration models such as those depicted in FIGS. 1-4 may be tailored as necessary or desirable to illustrate the effectiveness of individual oral care products (e.g., dentifrices), or of multiple oral care products in a comparative manner, at inhibiting dental erosion. The models may be effective for qualitative measurements, quantitative measurements, or both. Specifically, in one example embodiment, performance differences among multiple oral care products may be observed visually when a substrate coated with treated or untreated, simulated dental enamel is subjected to an acid challenge.

Figure 5:
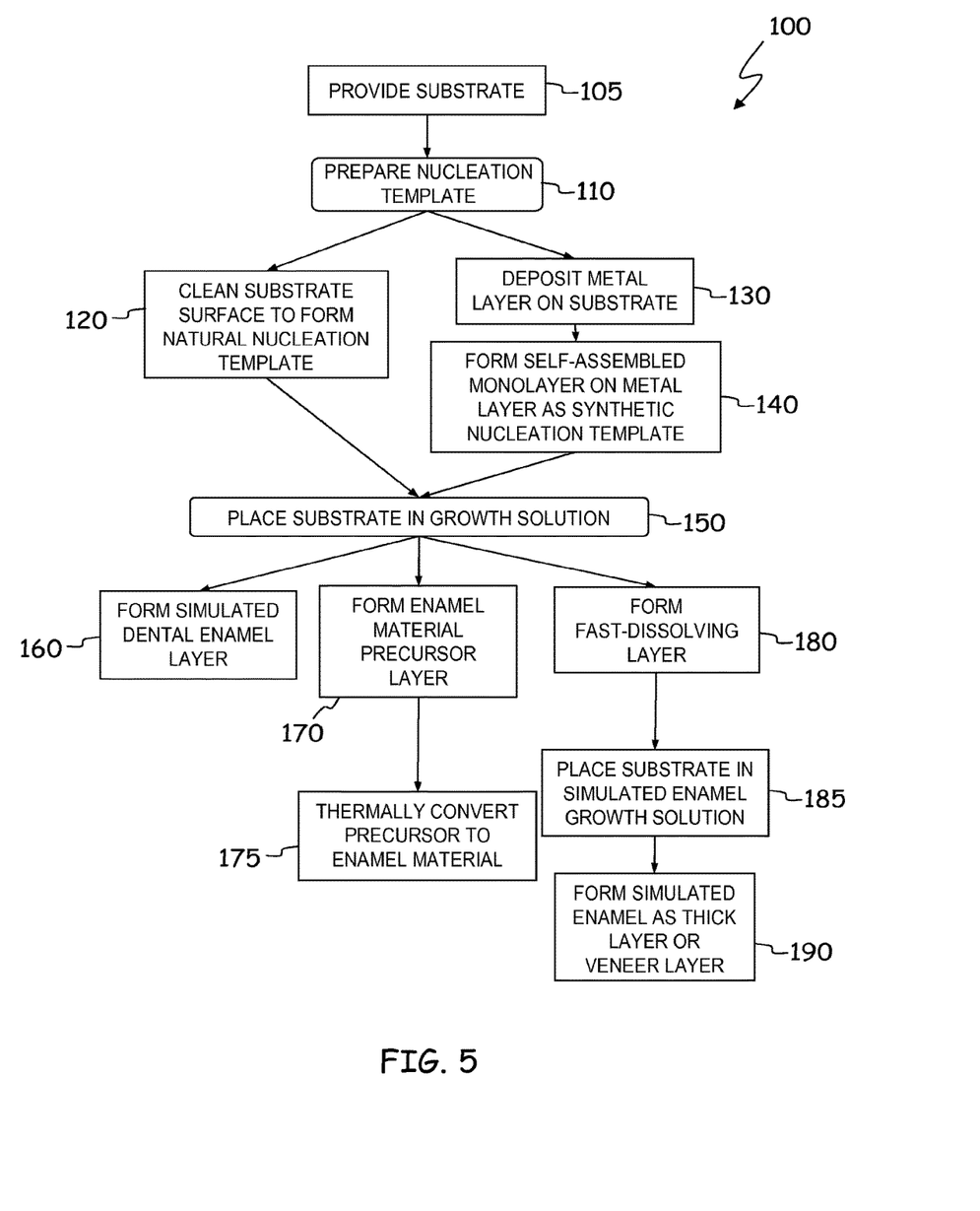
FIG. 5 is a flowchart of example methods for preparing demonstration models according to one or more embodiments.
Figure 6:
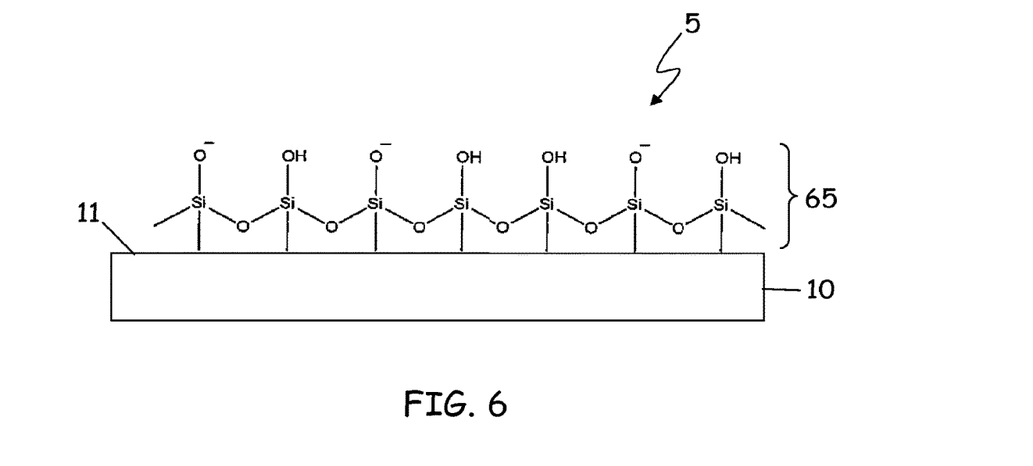
FIG. 6 is a side view of a first example natural nucleation template for simulated dental enamel layers.

Example methods for preparing demonstration models according to one or more example embodiments shown and described above are illustrated by the flowchart depicted in FIG. 5. In methods 100 for preparing demonstration models, a substrate, described above, is provided in step 105. A substrate surface of the substrate may provide a natural nucleation template for growth of a layer structure comprising a simulated dental enamel layer on the substrate, or a synthetic nucleation template may be grown on the substrate surface. In example methods, preparation of the nucleation template is shown as step 110 in FIG. 5. Both natural and synthetic nucleation templates are effective for supporting the simulated dental enamel layers. An example natural nucleation template 5 is depicted in FIG. 6 as native silanol groups 65 on a substrate surface 11 of a substrate 10, where the substrate is a material such as glass or quartz. The natural nucleation template 5 requires no preparation, except that the substrate surface may desirably be cleaned, shown as step 120 in FIG. 5. The precise structure of any natural template depends on the substrate itself. It will be understood, therefore, that alternative substrates, for example polymer films or tapes, also may possess natural nucleation templates having structures that differ from the silanol template of FIG. 6 but are nonetheless suitable for growth of simulated dental enamel thereon.

Figure 7:
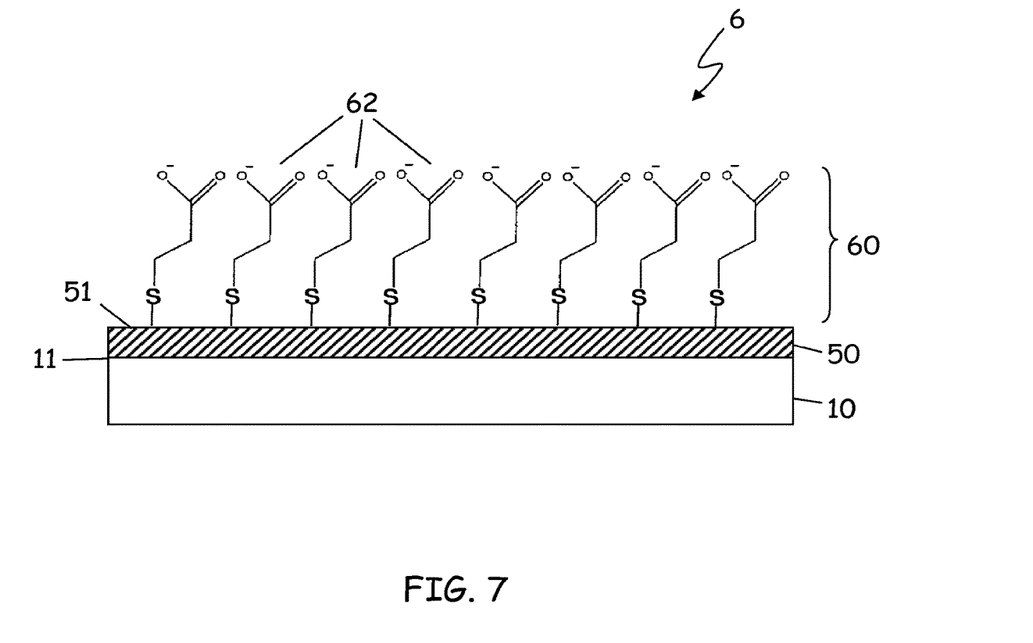
FIG. 7 is a side view of a second example synthetic nucleation template for simulated dental enamel

An example synthetic nucleation template 6 is depicted in FIG. 7 as a cross-section of an ordered, two-dimensional array of carboxyl groups 62 produced by self-assembly of carboxylated thiols on a metal-layer surface 51 of a metal layer 50 to form a self-assembled monolayer 60 on the metal-layer surface 51. The metal layer 50 may comprise gold or a gold alloy, for example, deposited on a substrate surface 11 of a substrate 10. Not to be limited by theory, it is believed that synthetic nucleation templates such as the synthetic nucleation template 6 shown in FIG. 7 reproducibly enhance formation of rugged simulated enamel layers. However, in some example embodiments, to adhere the self-assembled monolayer 60 to the substrate surface 11, the metal layer 50 is deposited first. The metal layer 50 may comprise gold or a gold alloy, for example.

To prepare an example synthetic nucleation template 6, the substrate 10 first may be coated with a metal layer 50 having a thickness of about 10 A to about 1000 A. This step is shown as step 130 in FIG. 5. Then, in step 140, a self-assembled monolayer 60 is formed on a surface of the metal layer 50, opposite the substrate 10. In example embodiments, gold is chosen for the metal layer 50 because of its high affinity to monolayer-forming groups such as long-chain thiols. However, it will be understood that any metal may be used that has a surface capable of bonding with organic functional groups that can arrange to form a self-assembled monolayer on the surface. The metal layer 50 may be deposited by any means known in the art of metal deposition, including, but not limited to, sputtering, evaporation, pulsed-laser deposition, chemical vapor deposition, combinations thereof, or other similar techniques. Thereupon, the metal layer 50 is exposed to a solution comprising molecules that each have a reactive end and a chain end and are amenable to forming self-assembled monolayers. Example molecules include, but are not limited to, functionalized thiols. One particular, non-limiting example of a functionalized thiol is a carboxyl-terminated alkyl thiol. The reactive end of the molecule bonds to the metal layer 50, and the chain end of the molecule extends above the metal layer 50, typically forming an angle of 0° to 60° offset from perpendicular to the gold surface to which the reactive end is attached. The chain end may be terminated with a functional group such as carboxyl that imparts acidity to the surface of the self-assembled monolayer 60 facing away from the metal layer 50. Thereby, the self-assembled monolayer 60 acts as a two dimensional, ordered nucleation template on which a simulated dental enamel layer may be grown.

In an example embodiment, a synthetic nucleation template comprising a self-assembled monolayer may be grown on a gold surface by exposing the gold to a solution comprising 1 mM 11-mercaptoundecanoic acid in ethanol for a period of time such as about 24 hours at room temperature (25° C.±2° C.). In the resulting structure it is believed that sulfur atoms bond to gold, long-chain alkyl groups arrange in an ordered manner above the gold surface, and carboxyl terminal groups provide a nucleation template suitable for growth of a simulated dental enamel layer thereon.

After a natural or synthetic nucleation template is prepared on the substrate surface, the substrate may be exposed to a growth solution to form a first layer on the nucleation template, according to step 150 in FIG. 5. The first layer may comprise a mineral such as hydroxyapatite, amorphous calcium phosphate, fluorapatite, chlorapatite, or combinations thereof. In one embodiment comprising step 160, for example, the first layer may comprise a substantially homogeneous layer of simulated dental enamel material such as hydroxyapatite. The hydroxyapatite may be formed directly on the nucleation template to result in single-layer demonstration model 1 (see FIG. 1) on a natural nucleation template or a single-layer-on-monolayer demonstration model 3 (see FIG. 3) on a synthetic nucleation template.

The various layers comprising minerals such as hydroxyapatite and amorphous calcium phosphate may be prepared by solution growth. Example growth solutions may contain, for example, a source of calcium ion and a source of phosphate ion. The growth solutions may further comprise additives for adjusting pH, for example, acids, bases, buffers, or combinations thereof. Example sources of calcium ions may include calcium salts having sufficient water solubility to produce a reaction with a phosphate ion in a buffered aqueous solution. Suitable calcium salts in this regard include, but are not limited to, calcium chloride, calcium fluoride, calcium carbonate, calcium bromide, calcium iodide, calcium nitrate, calcium nitrite, calcium benzoate, calcium acetate, calcium formate, calcium chlorate, calcium perchlorate, calcium gluconate, calcium permanganate, calcium thiosulfate, calcium dithionate, calcium chromate, calcium azide, calcium ferrocyanide, calcium fumarate, calcium isobutyrate, calcium maleate, calcium methylbutyrate, calcium propionate, calcium quinate, calcium selenate, calcium thiocyanate, calcium valerate, and any other suitable calcium salt. Example phosphate ion sources may include phosphate compounds with sufficient water solubility to react with a calcium ion in a buffered aqueous solution. Suitable phosphate ion sources in this regard may include, but not be limited to, alkali metal phosphates; hydrogen phosphates or dihydrogen phosphates; salts such as magnesium biphosphate; ammonium phosphates, including quaternary ammonium phosphates such as tetramethylammonium phosphate or tetrabutylammonium phosphate; combinations of any of these; or any other source of phosphate ions. The mineral solution also may contain fluorides, carbonates, or combinations thereof.

Concentrations of the various ion sources may be chosen such that supersaturation in an aqueous solution is achieved with respect to the desired mineral phase. Without being limited by theory, it is believed that a sum of calcium ion concentration and the phosphate ion concentration below about 10 mM may favor formation of a crystalline mineral such as hydroxyapatite over formation of non-crystalline material such as amorphous calcium phosphate. Typically, the solution growth process favors formation of crystalline minerals such as hydroxyapatite over non-crystalline minerals such as amorphous calcium phosphate when the pH remains nearly neutral during the growth process. Thus, the buffered growth solutions in example embodiments for forming hydroxyapatite may have a pH near or equal to 7.0.

For example, hydroxyapatite, may be grown directly on a selected nucleation template by exposing the substrate to an aqueous solution comprising 4 mM calcium chloride ($CaCl_2$), 4 mM potassium dihydrogen phosphate ($KH_2PO_4$), 1 ppm sodium fluoride (NaF), and 20 mM HEPES buffer, adjusted with sodium hydroxide (NaOH) to a pH of about 7.0. A HEPES buffer, as used in this example, comprises a salt of 4-(2-hydroxyethyl)piperazine)-I-ethanesulfonic acid; however it will be understood that many other known buffers may be appropriate for growth of hydroxyapatite. In a further embodiment, increasing the sodium fluoride content of the growth solution may favor significant formation of fluoridated hydroxyapatite, fluorapatite, or combinations thereof as components of the simulated enamel. It is believed that the presence of moderate levels of fluoride (for example, 0.25 ppm to 10 ppm) and growth temperatures in the range of about 40° C. to about 100° C. may favor the formation of crystalline minerals over the formation of non-crystalline minerals, even when the sum of the calcium ion concentration and the phosphate ion concentration is slightly elevated to, for example, the range of about 10 mM to about 25 mM.

The substrate may be exposed to a mineral growth solution by any means effective for producing growth of a mineral film on the surface of the substrate. For example, the substrate may be immersed in a mineral growth solution, or the substrate may be dipped in the solution repetitively and allowed to dry between each dipping. Alternatively, the substrate may be sprayed with mineral growth solution. The exposure of the substrate to the mineral solution may occur at a slightly elevated temperature that may accelerate dissolution. If desired, a slightly elevated temperature such as, for example, 37° C., may be chosen to simulate biological conditions. The example hydroxyapatite layers may be grown until clearly visible, typically requiring an exposure period ranging from about 20 minutes to about 24 hours, depending on desired thickness. In an example embodiment, a growth period of about 16 hours may result in a hydroxyapatite layer with an average thickness of about 200 nm. The substrate is removed from exposure to the mineral solution and dried. The substrate may be exposed to the growth solution repetitively to produce a layer of a desired thickness or a desired level of apparent visual contrast between the mineral layer and a bare substrate surface.

Even nanometer-scale thickness (e.g., greater than about 25 nm) hydroxyapatite layers scatter ambient light well, and are consequently quite visible on a substrate when dry. However, not to be limited by theory, it is believed that direct preparation of visually homogeneous hydroxyapatite films may be complicated by sensitivities of the crystal-growth induction period both to convection and to small variations in surface energy. A higher level of reproducibility may be achieved by using one or more alternative preparation methods. In example alternative embodiments, growth of hydroxyapatite may be preceded by deposition of a precursor layer such as amorphous calcium phosphate.

Amorphous calcium phosphate may be grown by precipitation, for example, from an aqueous solution comprising a calcium salt and a phosphate salt. Not to be limited by theory, it is believed that increasing the sum of calcium ion concentration and phosphate ion concentration favors formation of amorphous calcium phosphate over formation of a crystalline mineral such as hydroxyapatite. In one example method, amorphous calcium phosphate may be grown in a solution, wherein the sum of the calcium ion concentration and the phosphate ion concentration is greater than about 10 mM. Without being limited to theory, it is believed that lower temperatures, for example, below about 40° C., also favor formation of amorphous layers over formation of crystalline layers. In an example method for growing an amorphous calcium phosphate layer, the aqueous solution may comprise about 8 mM calcium bicarbonate ($CaHCO_3$) and about 4.6 mM potassium dihydrogen phosphate ($KH_2PO_4$). Under such conditions, the amorphous calcium phosphate may be allowed to aggregate on the nucleation template of a substrate placed on the bottom of the solution container. Depending on desired thickness, mineral films may be allowed to grow until clearly visible, typically for a time period ranging from about 5 minutes to about 24 hours, alternatively from about 10 minutes to about 20 hours, alternatively from about 30 minutes to about 10 hours, or alternatively from about 1 hour to about 5 hours.

Referring back to the flowchart in FIG. 5, particularly to step 160, once the first layer is grown on the nucleation template, the substrate may be simply removed from the growth solution once a simulated dental enamel layer is formed. Thus, the first layer formed may function as the simulated dental enamel layer of the demonstration model. In example embodiments, the first layer may comprise hydroxyapatite. In a particular example embodiment, the first layer may be a substantially homogeneous layer of hydroxyapatite. Depending on the nucleation template, an example resultant structure of the demonstration model thus may resemble one of the structures depicted in either FIG. 1 or FIG. 3, as described above. The structure in FIG. 1, comprises a natural nucleation template, whereas the structure in FIG. 3, comprises a synthetic nucleation template.

Alternatively, an enamel precursor layer may be formed in the growth solution, according to step 170 in FIG. 5. The enamel precursor layer may comprise amorphous calcium phosphate, for example. Then, at least a portion of the amorphous calcium phosphate may be converted to crystalline hydroxyapatite by a thermal transformation process according to step 175 in FIG. 5. The thermal transformation process may comprise heating a layer of amorphous calcium phosphate, disposed on a nucleation template, in aqueous or anhydrous environment at a temperature above about 40° C. for a period of about 10 minutes to about 24 hours, depending on the desired degree of conversion. In example embodiments, the thermal transformation may be conducted in the range of about 40° C. to about 100° C.; however it is fully contemplated that the transformation could be conducted at extremely high temperatures up to 900° C. if desired, provided the substrate can withstand such high heat. In one embodiment, substantially all of the amorphous calcium phosphate layer is converted to hydroxyapatite. Herein, it will be understood that substantially all of the amorphous calcium phosphate is converted when the weight ratio of hydroxyapatite to amorphous calcium phosphate is at least 10:1. Not intended to be limited by theory, it is believed that because of a relatively short induction period, hydroxyapatite layers derived from amorphous precursors exhibit improved uniformity over a homogeneous layer of hydroxyapatite grown according to the solution growth technique described above. In example embodiments, the thermally converted first layer functions as a simulated dental enamel layer in the demonstration model. Depending on the nucleation template, an example resultant structure of the demonstration model thus may resemble one of the structures depicted in either FIG. 1 or FIG. 3, as described above. The structure in FIG. 1, for example, comprises a natural nucleation template, whereas the structure in FIG. 3, for example, comprises a synthetic nucleation template.

Demonstration models having enhanced bilayer structures may be formed by first depositing a fast-dissolving layer on a natural or synthetic nucleation template, both described above, according to steps 105 through 150 of FIG. 5 and then removing the substrate from the growth solution when a fast-dissolving layer is formed, depicted as step 180. Then, at step 185 a second layer is grown on at least part of a surface of the fast-dissolving layer. As an example, the fast-dissolving layer may comprise amorphous calcium phosphate and the second layer may comprise hydroxyapatite (i.e., simulated dental enamel), both grown according to example methods described above. The second layer may comprise a thick layer or a thin veneer layer of hydroxyapatite. In example embodiments, growth of the second layer to form a simulated dental enamel layer according to step 190 may comprise exposing the substrate and first layer to a second growth solution, such as a solution described above for growth of hydroxyapatite, for a time sufficient to produce a second layer of a desired thickness. When the desired thickness is reached, the substrate may be removed from the second growth solution. Depending on the nucleation template, an example resultant structure of the demonstration model thus may resemble the bilayer demonstration model 2, shown in FIG. 2 on a natural nucleation template, or the bilayer-on-monolayer demonstration model 4, shown in FIG. 4 on a synthetic nucleation template.

Demonstration models comprising enhanced bilayer structures prepared according to methods comprising steps 180, 185, and 190 are especially advantageous for use in visual demonstrations, particularly when the first layer is chosen so that it dissolves in acid faster than the second layer. In one example embodiment, a demonstration model may be prepared according to a method comprising steps 180, 185, and 190, wherein the first layer may comprise amorphous calcium phosphate and the second layer may comprise a thin, veneer layer of hydroxyapatite. When such a demonstration model is exposed to an acid challenge solution, described below, initially the thin hydroxyapatite second layer dissolves at an initial dissolution rate. Once the acid challenge solution penetrates the hydroxyapatite layer to reveal amorphous calcium phosphate underneath, the dissolution rate increases substantially. Not to be limited by theory, it is believed that the increase in dissolution rate results because amorphous calcium phosphate is less resistant to acids than is hydroxyapatite. The amorphous calcium phosphate layer would be expected to dissolve noticeably more quickly and more thoroughly in a given amount of time than would a homogeneous layer of hydroxyapatite. Visual impact of a demonstration is directly related to the amount of material dissolved in the acid challenge solution, because the dissolution of layers such as simulated dental enamel layers produces a visual contrast between remaining layers and bare substrate. Thus, a demonstration conducted with a demonstration model having an enhanced bilayer comprising an amorphous calcium phosphate first layer and a hydroxyapatite (simulated dental enamel) second layer would be expected to produce faster results with increased visual impact over the results from demonstration models comprising single-layer simulated dental enamel layers.

Optionally, one or more coloring agents may be added to one or more of the layers or layer structures described above to enhance the visual impact of demonstrations conducted using the example demonstration materials as shown and described above herein. Optionally, multiple mineral layers may be grown consecutively on top of each other, such that each layer comprises a coloring agent of a slightly different shade or hue, each as defined above. Coloring agents may include, as non-limiting examples, dyes, pigments, opacifiers, combinations thereof, and any other additive both compatible with the layers of the demonstration model and effective at imparting color to the layers. Further example coloring agents may comprise chemical compounds capable of indicating the presence of components of the simulated dental enamel layers. One such example coloring agent is Alizarin Red, which indicates the presence of calcium. The coloring agents may be added to the mineral layer growth solutions described above. In one embodiment, the simulated enamel layers may be grown by successive immersions or dips in mineral growth solutions, each of which solutions comprises a different coloring agent. Within the resultant demonstration model, a composite structure of individual layers of varying shades or hues is formed. The composite structure is amenable to quantitatively illustrating progression of erosion when the demonstration model is used in a visual demonstration. Extent of erosion after an acid challenge, for example, would be evidenced by the color of the layer remaining after the challenge.

Demonstration models prepared according to example embodiments, as shown and described above may be used as visual aids to illustrate comparative effectiveness among selected oral care products (e.g., dentifrices) at preventing acid-related dental erosion. As used herein, an oral care product is "effective" at preventing dental erosion to the extent that a first sample of simulated dental enamel treated with the oral care product exhibits less erosion when subjected to an acid challenge than does a second sample of simulated dental enamel, having identical structure to the first sample, but subjected to the same acid challenge without being treated with any oral care product. These example visual illustrations may be presented or shown to potential consumers, customers, dental practitioners, health officials, regulators, or other interested persons. Not to be limited by theory, but it has been found that use of the demonstration models described herein are particularly advantageous over use of, for example, actual teeth such as from humans or bovines, because actual teeth become worn over time. Moreover, it is believed that actual teeth portray the desirable effects of erosion-preventive oral care products less accurately than do prepared demonstration models such as the demonstration models described and illustrated above.

Moreover, the demonstration models according to embodiments described above can be reproducibly formed, thereby lending themselves to highly objective comparisons when untreated or when treated with oral care products.

In an example method for demonstrating the effectiveness of an oral care product comprising a dentifrice, one or more demonstration models comprising a simulated dental enamel layer, according to a method shown and described above, may be used. If a plurality of models are used, the models may be on a plurality of substrates. In an alternative embodiment, a single substrate comprising a simulated dental enamel layer may be scored or otherwise marked to provide boundaries in the simulated dental enamel layer, effectively providing a plurality of models on the single substrate. Thus, subsequent stages of the demonstration method may be performed on only a portion of the simulated dental enamel layer or on the entire simulated dental enamel layer, as desired.

The models may be rinsed with purified water and then treated with a selected oral care product. Alternatively, a model may be left untreated so as to funcation as a control sample in a visual demonstration. In example embodiments, the oral care product may comprise a toothpaste or a mouthwash, but it will be understood that the use of the demonstration models is not limited to only toothpastes and mouthwashes. For example, the oral care product may comprise a solution that includes an active ingredient being investigated for use in a consumer product. The rinsing may be accomplished by quickly dipping one or more of the demonstration models into the water and quickly removing the one or more models from the water. The dipping and removal may occur, for example, in the course of about 1 to about 5 seconds.

Methods for treating the demonstration models with an oral care product depend on the phase characteristics of the oral care product being tested. If the oral care product is a toothpaste, for example, the treatment may comprise, for example, immersing one or more of the demonstration models in a slurry comprising the toothpaste. Additionally, the slurry may further comprise water, an artificial-saliva mixture, or combinations thereof. Example artificial-saliva mixtures may comprise aqueous solutions containing calcium ions, phosphate ions, fluoride ions, buffers, enzymes, or combinations of any of these. Example slurries may comprise, for example, 1 part oral care product and from about 3 parts to about 10 parts artificial saliva. If a liquid oral care product is tested, for example, a mouthwash, the example treatment method may comprise immersing the one or more of the demonstration models in undiluted product or a product slurry. In one example embodiment, the immersion time should approximate the recommended time for personal use of the oral care product in a consumer setting. Example immersion times may include, but not be limited to, from about 0 seconds to about 10 minutes, from about 5 seconds to about 4 minutes, or from about 30 seconds to about 2 minutes. In one embodiment, wherein multiple demonstration models may be prepared and treated with multiple oral care products for comparison among the products, the immersion time in the product slurry or undiluted liquid product preferably is controlled among the demonstration models. In another embodiment, multiple demonstration models may be prepared and treated with the same oral care product to compare effectiveness as a function of time of exposure, but the immersion times may be different. After the one or more demonstration models are treated with the oral care product, the models may be rinsed with purified water.

Treated or untreated demonstration models then may be subjected to an acid challenge to demonstrate erosion. Generally, acid challenge involves exposure of the simulated dental enamel to a corrosive influence that simulates an acidic environment inside the oral cavity. Thus, in example embodiments, dilute solutions of weak acids are used. In one example embodiment, the acid challenge may comprise immersing the demonstration models in an acid challenge solution. For example, the acid challenge solution may comprise an aqueous solution containing 1% by weight citric acid. The length of exposure to the acid challenge (i.e., erosion challenge) may be varied to maximize differences such as, for example, visual differences, depending on which products are tested. In example embodiments, the length of acid exposure may range from about 0 seconds to about 24 hours, from about 5 seconds to about 15 hours, or from about 10 seconds to about 10 hours; however, to facilitate short visual demonstrations for consumers, the length of acid exposure may be from about 0 seconds to about 10 minutes, from about 5 seconds to about 8 minutes, or from about 10 seconds to about 5 minutes. As one example, to directly compare the effectiveness of two or more oral care products, the acid challenge time preferably is approximately identical for all treated demonstration models. As another example, erosion-preventive effectiveness of a single oral care product may be demonstrated with respect to time of acid exposure by exposing each demonstration model to acid for various amounts of time. Following the acid challenge, the models may be rinsed, dried, or both. Rinsing may comprise quickly dipping one or more of the models in purified water as described above. Drying may comprise quickly dipping one or more of the models in methanol, followed by exposure to air, heat, or both. It will be understood, however, that the exposure times above have been described for illustration purposes only, and not for limitation. As such, it is understood that the exposure times may comprise any conceivable time as desired.

As noted in the definition above, the term "oral care product" is not limited to formulations suitable for consumer use but includes also specific compounds that may be desirable ingredients of consumer products. Thus, in one example embodiment, erosion preventive effectiveness of phosphate compounds may be demonstrated. Not to be limited by theory, it is believed that certain phosphate compounds may impart increased erosion-preventive effectiveness through the ability of their phosphate groups to chelate calcium in mineral layers such as hydroxyapatite. Example phosphate compounds include, but are not limited to, inorganic polyphosphates such as sodium acid pyrophosphate, sodium tripolyphosphate, and sodium hexametaphosphate; polyphosphorylated inositol compounds such as phytic acid and sodium phytate; alkyl phosphates or alkali metal, ammonium, or alkaline earth metal phosphate salts thereof; and combinations of any of these.

In an example method, a demonstration model according to one or more embodiments described above may be used for demonstrating erosion-preventive effectiveness of phosphate compounds. For example, the demonstration model may comprise a uniform layer of hydroxyapatite on at least a test portion of a substrate such as, for example, a single-sided adhesive tape. At least the test portion may be treated, for example, by soaking at least the test portion for about 15 seconds in an aqueous solution comprising an amount of sodium hexametaphosphate, for example, about 2% by weight. The treated substrate and layer may be rinsed one or more times with fresh tap water. Optionally, the layer may be soaked in a solution of a calcium-specific dye such as, for example, a 0.25% by weight solution of Alizarin Red. Calcium ions combine with Alizarin Red and form a bright red color. A deep red color would indicate a high level of calcium ions and thus a low level of chelation of calcium in the hydroxyapatite. Thus, it is believed the red color level can be used during a demonstration to predict the level of chelation of the hydroxyapatite by the sodium hexametaphosphate and, furthermore, to predict erosion-preventive effectiveness of the sodium hexametaphosphate, even before the layer is exposed to an acid solution. The chelated layer of hydroxyapatite then may be exposed to an acid solution and optionally may be rinsed.

In a further example embodiment, erosion-preventive effectiveness may be demonstrated on simulated dental enamel layers treated with one or more ingredients selected from alkyl phosphates, stannous fluoride, one or more surfactants, or combinations of these. Not to be limited by theory, it is believed that alkyl phosphates may impart increased erosion-preventive effectiveness through the ability of their phosphate groups to chelate with calcium in mineral layers such as hydroxyapatite and that surfactants may further increase the erosion-preventive effectiveness. The surfactants are believed to impart further chelation of the alkyl phosphates with the mineral layers. Moreover, hydrophobic tail groups of the surfactants may further increase erosion-preventive effectiveness by imparting hydrophobicity to the mineral layer surface after treatment with the alkyl phosphates. Example alkyl phosphates include, but are not limited to, lauryl phosphate; laureth 1-phosphate; laureth-3 phosphate; trilaureth-4 phosphate; sodium, potassium, or ammonium salts of any of these; and combinations of any of these. Examples of effective surfactants in this regard include, but are not limited to, sodium lauryl sulfate, sodium lauryl sarcosinate, sodium lauroyllactylate, sodium lauroyl glutamate, sodium methyl cocoyl taurate, sodium cocoyl glycinate, cocamidopropyl betaine, lauryl betaine, arginine cocoate, potassium cocoate, or combinations of any of these. Specific example surfactants include sodium cocoyl glycinate. Surfactants also may interact with stannous fluoride, a common dentifrice ingredient, in a manner that may increase erosion prevention generally and may increase visual impact of demonstrations involving treatments with stannous fluoride. Not to be limited by theory, but it is believed that certain surfactants not only increase surface hydrophobicity of mineral layers but also chelate strongly with stannous fluoride. Specific example surfactants for interaction with stannous fluoride include sodium cocoyl glycinate, arginine cocoate, and potassium cocoate.

In an example method for demonstrating erosion-preventive effectiveness of alkyl phosphates, a demonstration model may be used. The demonstration model may comprise, for example, a uniform layer of hydroxyapatite disposed on one side of a tape substrate. At least a test portion of the layer may be exposed to alkyl phosphate by soaking, for example, for about 15 seconds in an aqueous solution comprising an amount of alkyl phosphate, for example, about 2% by weight. At least the test portion of the layer may be treated further with an optional surfactant, stannous fluoride, or both. In one embodiment, the treatment with chelation enhancer may involve soaking the layer in a solution comprising the surfactant and, for example, a 0.5% by weight solution of stannous fluoride. The soaked layer may be rinsed one or more times with fresh tap water. Optionally, the layer may be soaked in a solution of a calcium-specific dye such as, for example, Alizarin Red. The dye may be present in a small amount such as, for example, in a 0.25% by weight solution. Again the red color level can be used during the demonstration to predict the level of chelation of the hydroxyapatite by the alkyl phosphate and its erosion preventive effectiveness, even before the layer is exposed to an acid solution. As desired, hydrophobicity of the hydroxyapatite layer may be assessed by observing placing a drop of water on the surface of the layer and observing if the drop of water spreads. This observation may be predictive of erosion-preventive effectiveness even before the acid challenge. The chelated layer of hydroxyapatite then may be exposed to an acid solution and optionally rinsed.

The effectiveness of any oral care product at preventing dental erosion (i.e., the "erosion preventive effectiveness") may be inferred from the amount of the simulated dental enamel layer remaining on the substrate of the demonstration model after the treatments, the exposure to the acid challenge, and the optional rinsing and drying. Thus, a demonstration model treated with a highly effective oral care product will retain a substantial amount of the simulated dental enamel layer after exposure to the acid challenge. Conversely, a demonstration model treated with a less effective oral care product will retain less of the simulated dental enamel layer after exposure to the acid challenge. In some embodiments, an untreated demonstration model may retain less of the simulated dental enamel after exposure to the acid challenge than the model treated with an oral care product. In another example embodiment, an untreated demonstration model may be configured such that after exposure to an acid challenge it is substantially free of simulated dental enamel layer so as to maximize the visual impact of the demonstration. If coloring agents were used during the preparation of the simulated enamel layers, as in embodiments described above, the extent of the simulated erosion may be qualified or highlighted further through observations of the specific color or colors of the mineral layers remaining after exposure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Though particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of preparing a demonstration model, the method comprising:
    exposing a substrate comprising a nucleation template to a first aqueous solution until a
        first mineral layer visibly forms on the nucleation template through heterogeneous nucleation; wherein the first aqueous solution comprises a calcium salt and a phosphate salt; and
    removing the substrate from exposure to the first aqueous solution,
    wherein the first mineral layer comprises amorphous calcium phosphate and the method further comprises heating the first mineral layer at a temperature from 40° C. to 100° C. to convert substantially all of the amorphous calcium phosphate to hydroxyapatite.

2. The method of claim 1 wherein the substrate is selected from the group consisting of molded polymer articles, polymer films, polymer tapes, silica, quartz, glasses and combinations thereof.

3. The method of claim 2 wherein the substrate comprises silica.

4. The method of claim 1 wherein the first mineral layer is from about 10 Å to about 100 nm thick.

5. The method of claim 1 wherein the first mineral layer has a thickness from about 10 Å to about 500 μm.

* * * * *